United States Patent [19]
Thompson et al.

[11] Patent Number: 6,132,977
[45] Date of Patent: Oct. 17, 2000

[54] MEASUREMENT OF A CNS PROTEIN IN CEREBROSPINAL OR AMNIOTIC FLUID

[75] Inventors: Peter M. Thompson; Nora Perrone-Bizzozero, both of Albuquerque, N. Mex.

[73] Assignee: University of New Mexico, Albuquerque, N. Mex.

[21] Appl. No.: 09/042,152

[22] Filed: Mar. 13, 1998

[51] Int. Cl.[7] .................. A61K 39/395; A61K 39/00; A61K 35/30; G01N 33/53; G01N 33/557

[52] U.S. Cl. .................. 435/7.1; 424/141.1; 424/142.1; 424/184.1; 424/570; 435/7.1; 435/960; 435/971; 436/517

[58] Field of Search ............... 424/141.1, 142.1, 424/184.1, 570; 435/7.1, 960, 971; 436/517

[56] References Cited

U.S. PATENT DOCUMENTS 5,693,476  12/1997  Scheller .................................. 435/7.1

FOREIGN PATENT DOCUMENTS

WO 98/38210  9/1998  European Pat. Off. ........ C07K 14/00

OTHER PUBLICATIONS

Nemoz–Gaillard et al. 1998. FEBS Letters. 425:6–70.
Shimohama et al. 1997. Biochemical and Biophysical research Comm. 236:239–242.
Chemical Abstracts a publication of the Chemical Abstracts Service (CAS), vol. 105, No. 25, Dec. 22, 1986.
Burdett et al., "Proteins of Human Amniotic Fluid. II. Mapping by Two–Dimensional Electrophoresis," *Clinical Chemistry*, vol. 28, No. 4, 1982.
Catscias et al., "Differential Expression of the Presynaptic Protein SNAP–25 in Mammalian Retina," *Journal of Neuroscience Research*, 33: 1–9 (1992).
Csernansky et al., "Progressive Neurodegeneration after Intracerebroventricular Kainic Acid Administration in Rats: Implications for Schizophrenia?" *Biol Psychiatry*, 1998: 44: 1143–1150.
Dermer et al., "Enhancement Techniques for Detecting Trace and Fluid–Specific Components in Two–Dimensional Electrophoresis Patterns," *Clinical Chemistry*, vol. 28, No. 4, 759–765, 1982.
Fatemi et al., "Differential expression of synaptosome–associated protein 25 kDa [SNAP–25] in hippocampi of neonatal mice following exposure to human influenza virus in utero," *Brain Research* 800 (1998) 1–9.
Geddes et al., Lesions of Hippocampal Circuitry Define Synaptosomal–Associated Protein–25 (Snap–25) as a Novel Presynaptic Marker, vol. 38, No. 2, 515–525, 1990.
Hess et al., "Spontaneous Locomotor Hyperactivity in a Mouse Mutant with a Deletion Including the Snap Gene on Chromosome 2," *The Journal of Neuroscience*, Jul. 1992, 12(7): 2865–2874.
Heyser et al., "Coloboma hyperactive mutant exhibits delayed neurobehavioral developmental milestones," *Developmental Brain Research* 00(1995) 000–000.

(List continued on next page.)

*Primary Examiner*—James C. Housel
*Assistant Examiner*—Ja-Na Hines
*Attorney, Agent, or Firm*—Jagtiani & Associates

[57] ABSTRACT

SNAP–25 (synaptosomal associated protein) is purified from cerebrospinal or amniotic fluid for immunoassay and quantitation. Quantitation of these proteins is useful in the diagnosis and monitoring of brain disorders and diseases such as schizophrenia and Alzheimer's.

8 Claims, 8 Drawing Sheets

OTHER PUBLICATIONS

Ibsen et al., "Quantification of the D2–Glycoprotein in Amniotic Fluid and Serum from Pregnancies with Fetal Neural Tube Defects," *Journal of Neurochemistry*, vol. 41, No. 2, 1983.

Jacobsson et al., "Differential subcellar localization of SNAP–25a and SNAP–25b RNA transcripts in spinal motoneurons and plasticity in expression after nerve injury," *Molecular Brain Research* 37 (1996) 49–62.

Jørgenson et al., "Synaptic Remodeling and Free Radical Formation after Brain Contusion Injury in the Rat," *Experimental Neurology* 144, 326–338 (1997), Article No. EN966372.

Jørgenson, Ole Steen, "Polypeptides of the Synaptic Membrane Antigens D1, D2, and D3," *Biochimica et Biophysica Acta*, 581 (1979) 153–162.

Jørgenson, Ole Steen, "Localization of the Antigens D1, D2 and D3 in the Rat Brain Synaptic Membrane," *Journal of Neurochemistry*, 1976, vol. 27, pp. 1223–1227.

Jørgenson, Ole Steen, Neural Cell Adhesion Molecule (NCAM) as a Quantitative Marker in Synaptic Remodeling, *Neurochemical Research*, vol. 20, No. 5, 1995, pp. 533–547.

Jørgenson et al, "Synaptic Plasma Membrane Antigen D2 Measured in Human Cerebrospinal Fluid by Rocket–Line Immunoelectrophoresis, Determination in Psychiatric and Neurological Patients," *Scandinavian Journal of Immunology*, 4, Supp. 2, 25–30, (1975).

Jørgenson, Ole Steen, "Fetal Neural Tube Defects Detected by Rocket–on–Line Immunoelectrophoresis of Aminiotic Fluids," *Clinica Chemica Acta.*, 124 (1982) 179–186.

Lustig et al., "Ontogeny, sex dimorphism, and neonatal sex hormone determination of synapse–associated messenger RNAs in rat brain," *Molecular Brain Research*, 20 (1993) 101–110.

Nabokina et al., "Intracellular Location of SNAP–25 in Human Neutrophils," *Biochemical and Biophysical Research Communications* 239, 592–597 (1997), Article No. RC977515.

Oyler et al., "The Identification of a Novel Synaptosomal–associated Protein, SNAP–25, Differentially Expressed by Neuronal Subpopulations," *The Journal of Cell Biology*, vol. 109, 1989.

Thompson et al., "Measuring synaptosomal associated protein–25 kDa in human cerebral spinal fluid," *Journal of Psychiatric Research* 32, 91998) 297–300.

CSF

MEASUREMENT OF A CNS PROTEIN IN CEREBROSPINAL OR AMNIOTIC FLUID

BACKGROUND OF THE INVENTION

The invention relates to the identification and quantitation of a central nervous system (CNS) protein in cerebral spinal fluid and amniotic fluid.

Field of Art and Discussion of Related Art

Certain CNS proteins are of interest as markers and trackers of brain pathophysiology, especially in the areas of synaptogenesis and synaptic vesicle release. Neurotransmitter release is, however, a complicated process involving many different proteins (*Nature* 355: 409–415, 1992), some of which are SNAP-25 (synaptosomal associated protein-25 kDa), VAMP/synaptobrevin (1,2), syntaxin (1a, 1b), neurexin (1,2), synapsin (1,2), and synaptophysin.

The understanding of normal brain physiology is moving at great speed. One area that is especially important to diagnosing and treating mental illnesses is the pathway for release of neurotransmitters. In this process proteins called vesicular snares (V-snares) attach to plasma membrane and release neurotransmitter (*Nature* 335: 409–415, 1992). One T-snare that is associated with mental illness is SNAP-25. This protein is found predominately in brain tissue of neuronal origin (*Molecular Brain Research* 1: 1–16, 1986). The other major brain tissue (glial cells) is non-neuronal and SNAP-25 has not been associated with this tissue. SNAP-25 in monomeric form is 25 kDa, but can be found in vivo as a dimer, or associated with other synaptic proteins (e.g. syntaxins).

SNAP-25 appears to be particularly important in the pathophysiology of schizophrenia and other major brain disorders, because of its known dual role in synaptic vesicle release and synaptogenesis (*J. Neuroscience* 12: 2865–2874, 1992; *PNAS USA* 92: 1510–1514, 1995). Also, it has been shown that both SNAP-25 and GAP-43 (*Mol. and Chem. Neuropath.* 23: 1–11, 1994) have altered levels in post mortem brains of schizophrenic patients. These or other proteins involved with synaptic vesicle release and synaptogenesis may be strongly associated with brain function and behavior.

Mental illness (as defined e.g., by Andreasen and Black (Andreasen, N. C., Black, D. W. Introductory textbook of psychiatry 1991, American Psychiatric Press, Inc.) has a profound effect on public health, but psychiatry has had difficulty developing biological assays to diagnosis and follow them. Neuroscientific interest has particularly been aroused by the possibility of correlating levels of these and other CNS proteins with specific brain pathologies and with different stages of illness, such as identifying brain changes in schizophrenia and other major brain disorders, such as Alzheimer's disease and clinical depression. Although impressive gains have been made in neuroimaging and brain electrophysiology, molecular and cellular markers of schizophrenia and other brain disorders have lagged. There are no consistent known biochemical markers for schizophrenia pathophysiology, and none that reflect effectiveness of a course of treatment. There is a lack of complete animal models of schizophrenia and lack of in vitro assays for physiologically-relevant neuronal proteins. Further, obtaining material to perform biological assays has been a constant problem in schizophrenia and other brain disorder research. Peripheral assays including platelet levels, peripheral nerve biopsy, and neurohormone levels have not yielded informative data. More central assays such as estimating neurotransmitter levels in cerebral spinal fluid (CSF) have been only marginally more informative (*Ann, Clin. Biochem* 27: 425–435, 1990). Direct methods of studying neuronal tissues such as brain biopsies are prohibitively destructive due to loss of brain tissue. These impediments have limited the most potentially informative studies to post-mortem studies.

These difficulties have hindered research on the identification of neuronal proteins and their roles in the molecular pathways involved in pathological changes in the brain.

SUMMARY OF THE DISCLOSURE

The invention accordingly provides methods for the immunological identification and quantitation of SNAP-25 which is normally present in certain body fluids. In particular, a procedure is disclosed for the detection and quantitation of synaptosomal associated protein 25 kDa (SNAP-25) level in a biological fluid, especially cerebrospinal fluid and amniotic fluid. The quantitated levels of SNAP-25 serve as a diagnostic marker for some mental illnesses such as Major Depression, Alzheimer's Disease and Schizophrenia, and are also useful for monitoring such mental illnesses.

The invention is predicated on the discovery that native SNAP-25 can be purified from sample fluids by separation of albumin and immunoglobulins from the fluid and concentration of remaining protein. The recovered protein is sufficiently concentrated with respect to CNS protein to permit immobilization and immunoassay for the protein.

The methods reliably identify SNAP-25 proteins in human cerebrospinal fluid (CSF) and amniotic fluid (AF), and permit clinical comparison of normal and ill subjects for abnormal protein concentrations. Comparison of protein concentrations of patients in varying stages of illness for diagnosis and evaluation of treatment is of particular interest.

BRIEF DESCRIPTION OF THE DRAWING

FIG. 1 illustrates Western blots of CSF and AF stained for brain specific protein antibodies. In panels A, B and C, each band represents an individual person.

Panel A is a Neural-Cell Adhesion Molecule (N-CAM) antibody in human CSF.

Panel B is a Synaptosomal Associated Protein 25 kDa (SNAP-25) antibody in human CSF.

Panel C is a Growth Associated protein 43 25 kDa (GAP-43) in human CSF.

Panel D is a Dopamine Receptor 4 antibody in human AF, CSF-cerebral spinal fluid, BH-human whole brain homogenate, and MW-molecular weight standard.

FIG. 3: A-Coomassie Blue stained blot. Lanes 1–3: 7.0 μg (total protein) SNAP-25 immunoprecipitate; Lane 4: 0.2 μg (total protein) CSF treated with Protein G and Blue Sepharose™; Lane 5: 0.3 μg (total protein) CSF treated with Protein G; Lane 6: 0.25 μg (total protein) CSF treated with Blue Sepharose™; Lane 7: 2.0 μg (total protein) untreated CSF. B-Visualization of SNAP-25 by Mab331 in CSF. Arrows indicate molecular weight (top to bottom in kDa), 66, 44, 30, 21.5, and 14.4. Protein G is a bacterial cell wall protein isolated from group g streptococci that binds the Fc region of mammalian immunoglobulins. Blue Sepharose™, a product made by Pharmacia Biotech Corp., is obtained by immobilizing Civachrone blue F3GA on Sepharose (purified agarose).

DETAILED DESCRIPTION OF THE INVENTION

The method of the invention comprises concentrating a normally dilute CNS protein in human CSF or AF by separation of albumin; immobilizing the concentrated protein on a suitable support; and reacting immobilized protein with anti-protein antibody, especially monoclonal antibody in any conventional immunoassay procedure. Preferably, the albumin-depleted fluid is further concentrated with respect to total protein content after removal of albumin by any conventional technique such as lyophilization, before immobilization and immunoassay. It is desirable to separate recovered proteins on the basis of molecular weight, as by electrophoresis, prior to immunoassay.

CSF is obtained in a conventional manner by clinical lumbar puncture of the spinal canal. Amniotic fluid is conveniently obtained routine by amniocentesis, which is usually performed between the 14th and 20th week of gestation. At this time, development of the brain is underway and SNAP-25 concentration is meaningful. 500 μl cerebral spinal fluid (CSF) and 1500 μl of amniotic fluid are sufficient for clinical analysis according to the invention. The fluid is then either immediately processed or stored frozen at least −20° C.

In a preferred embodiment of the invention, albumin is separated from the sample fluid by incubation with Sepharose™ beads, followed by separation of the beads from supernatant. The purified supernatant is then concentrated with respect to total protein content by any standard method such as lyophilization. A total protein content of not less than about 150 μg/ml is recommended for best results. The entire protein concentration is then measured, and immobilized on a suitable support such as a polyvinylidene-difluoride membrane for immunoassay.

Exemplary classes of CNS proteins identifiable by the process of the invention are those associated with synaptogenesis, the release of synaptic vesicles containing neurotransmitters, and nerve growth, such as those mentioned supra.

The pathway involved in the release of synaptic vesicles containing neurotransmitters encompasses numerous proteins. Alterations of proteins in the pathway could have predictably profound effects of neurotransmitter levels and behavior. As previously discussed, SNAP-25 is one of the most promising proteins for a significant role in the docking of neurotransmitter-containing vesicles. As with neurotransmitter-release proteins, alterations in the levels of nerve growth-associated proteins may have a major effect on neuronal organization and behavior.

One of the specific applications of the invention is to determine if brain proteins such as SNAP-25 has altered levels in the brains of patients with schizophrenia in various stages of the disease, as compared to normal controls. Determination of these altered levels then permits correlation with schizophrenia in various stages and provide a method for the diagnosis and treatment evaluation of this illness. Important stages for protein analysis are: (1) untreated and psychotic; (2) treated with a neuroleptic and in remission; and (3) treated with a neuroleptic and non-responsive to medication. It is contemplated that alteration of the levels of SNAP-25 in, for example, schizophrenia in the psychotic state, are diagnostic of schizophrenia, and permit an evaluation of treatment based on whether or not protein levels tend back toward normal. For example, SNAP-25 levels are lowered and in psychotic schizophrenia, as compared to normal controls.

A further particular application of this invention is to measure SNAP-25 levels in amniotic fluid, which are altered according to the morphological state of the fetus. The invention thus provides a method for the diagnosis of severe brain damage in fetuses, such as those with anencephaly and neural tube defects including spina bifida, and the subtle brain trauma accompanying Downs syndrome. Analysis of SNAP-25 in AF from fetuses with abnormal chromosomes and neural tube defects and comparison with normal age-matched controls provide methods for characterization of brain trauma in fetuses.

The subject invention accordingly results from the unexpected and entirely novel detection of SNAP-25 in body fluids, especially cerebrospinal fluid and amniotic fluid. This discovery provides the first demonstration that SNAP-25 is present in a non-neuronal area. The detection and quantitative measurements of SNAP-25 in such fluid in accordance with this invention is useful in confirming clinical diagnoses of Alzheimer's disease, multiple sclerosis, schizophrenia, and other mental illnesses.

EXAMPLES

Example I

Collection of CSF and AF

Patients with a clinical problem potentially caused by brain pathology are sent to the appropriate physician for the collection of CSF or AF.

CSF is collected by standard lumbar puncture. All referred patients are eligible, except where a medical contradiction exists, such as cerebral edema. Medical diagnoses have been completed by physicians in both research and non-research areas.

AF is collected by the usual clinical procedure which is amniocentesis.

Example II

Albumin Separation

Albumin makes up the major protein of cerebral spinal fluid and is the largest barrier to clear immunodetection of proteins. Albumin was separated by placing about 250 μl of Blue Sepharose™ beads (CL-6B #17-0830-01, Pharmacia Biotech AB, Uppsala Sweden) per 250 μl of CSF protein within an Epindorff tube and incubating for ten minutes at room temperature with rocking. The beads were then separated from the supernatant by centrifugation. For amniotic fluid, 1–5 ml was used per 500 μl of Sepharose™ beads.

Example III

Concentration of Protein in Albumin-Depleted Fluid

The purified supernatant was concentrated by standard lyophilization. Proteins were resuspended in 100 μl of buffer, e.g., phosphate-buffered saline. Protein concentration was determined by taking an aliquot of concentrated sample and placing it on PVDF membrane by standard dot blot procedure. The protein was visualized by staining with Coomassie brilliant blue dye. By comparing the intensity of the contrasted sample dot to that of a standard known protein the concentration of protein was determined.

Example IV

Transfer of Proteins to Polyvinylidenedifluoride (PVDF) Membrane

A) Western Blot

Processed fluid from Example III was placed in a slab electrophoresis apparatus either 1D or 2D electrophoresis. In this example, a 10% denaturizing SDS polyacrylamide gel was used. To each sample was added a GP 250 blue tracking dye as standard. The electrophoresis apparatus was run at 35 mA/gel for approximately four hours with water flow cooling at room temperature. At this point, the polyacrylamide gel was taken out of the slab electrophoresis apparatus. The proteins were transferred from the gel to a PVDF membrane (Biorad Corp. 0.20 membrane cat# 1620184) under electric field 25 mA/cm$^2$ and a buffer of pH 8.3 by standard Western blot technique. Transfers were made in a cold room at 4° C. Membranes were then stained with Coomassie brilliant blue for ten minutes followed by destaining in 50% methanol and 10% acetic acid for ten minutes.

B) Dot Blotting of Cerebral Spinal Fluid Proteins

After the proteins from Example III were concentrated an aliquot was loaded directly onto a PVDF membrane by pipetting the aliquot into one of 96 wells on the blotter. The apparatus was connected to a vacuum source so that the vacuum was pulled through the membrane and collected in a bottom piece while the protein remained in the membrane as per standard dot blotting procedure.

Example V

Immunodetection

After the blots from Example IV (Western and dot) were air dried, the membranes were blocked with blocking buffer containing 150 mM NaCl, 20 mM Tris, 0.5% TWEEN™ 20 (sabutan monolaurate polyoxyalkylene) and 10% nonfat powdered milk at pH 7.4 for one hour at room temperature. The blocking buffer was drained off and primary antibody was added. In this example, antibody to synaptosomal-associated protein-25 (SNAP-25) was a mouse monoclonal antibody diluted 1 to 500. Antibody to growth associated protein-43 (GAP-43) was a sheep monoclonal antibody diluted 1 to 50. Anti-SNAP antibody is obtainable from Sternberger Microclonals Incorporated, cat #SM181. Anti-GAP antibody was prepared from immunized sheep by standard methods for obtaining monoclonal antibody. Antibodies to other antigens, such as $NMDAR_1$ receptor, $GABA_A\alpha$ receptor, or Dopamine 4 receptor can be similarly detected. Following primary antibody incubation of one hour at room temperature, the blots were washed three times for ten minutes with blocking solution, each at room temperature, with mild agitation. Following the blocking solution wash, the blots were either stained by enhanced chemiluminescence (ECL) immersion technique, or by standard nitroblue tetrazolium/4-bromo-3-chloro-2-indoyl-phosphate (NBT/BCIP) methods. The ECL method comprises binding antigen to a secondary antibody conjugated to horseradish peroxidase. The horseradish peroxidase catalyzes the oxidation of luminol, which releases a photon measured by exposing the blot to X-ray film. Alternatively, a NBT/BCIP method comprising binding antigen to a secondary antibody conjugated to alkaline phosphatase is used. In this method, the phosphatase uses NBT/BCIP as a substrate, with columetric analysis of protein concentration.

For the NBT/BCIP method, secondary antibody was incubated with the sample for two hours at room temperature. This was followed by three washes in blocking solution for 15 minutes each, followed by two washes of ten minutes each in PBS-T pH 9.5.

The ECL method used required secondary antibody incubation for one hour at room temperature, followed by four washes of ten minutes each in PBS with 0.1% TWEEN-20. Following the final wash, the blot was subjected to x-ray film per standard immersion protocol.

After visualization, the blots were scanned into a computer using an image analysis scanner and suitable software. The intensity of the visualized band or blots was calculated, and these data statistically analyzed by covariance and t-test. Results are illustrated in FIG. 1.

Example VI

SNAP-25 Levels by Quantitative Western Blot

For Western blot, 1.0 ml aliquots of CSF or AF were incubated with 0.5 ml Blue Sepharose™ CL-6B beads (Pharmacia Biotech) at room temperature for 30 minutes. The CL-6B beads have an available albumin binding capacity of 5 mg/ml, which is used in excess to absorb the entire amount of albumin present in our samples. The beads were spun at a relative centrifugal force of 16,000 Xg for 1 minute and the CSF removed. The albumin-depleted CSF was then incubated with 0.1 ml Protein G beads (Pharmacia Biotech) for one hour at room temperature. Protein G beads have an IgG available binding capacity of 24 mg/ml. Protein G beads were removed by centrifugation as previously described.

To immunoprecipitate SNAP-25 from the CSF, CNBr-activated Sepharose 4B™ (Pharmacia Biotech) was bound to approximately 10 mg of monoclonal antibody SMI-81 (Sternberger Monoclonals), a monoclonal antibody to SNAP-25, per the manufacturer's protocol. Antibody-bound CNBr-4B beads were then added to the 1.0 ml CSF samples purified of albumin and immunoglobulin at room temperature with shaking for 1 hour. The beads were then spun as before, and washed in phosphate buffered saline (PBS). Bound antigen was eluted with 2.5 M NaCl.

20 mM dithiothreitol was added to a solubilization buffer containing 0.25% β-mercaptoethanol. Twenty microliter aliquots of CNBr bead eluant and CSF were then run on an 8–16% Tris-glycine gradient SDS polyacrylamide gel (Nova Corp). Following electrophoresis, the protein was transferred to a PVDF membrane (Immobilon-p™ Millipore Corp) by electroblotting (Towbin et al., *Proc. Natl. Acad. Sci.* 76:4350, 1979). The blots were blocked in 10% powdered milk in TTBS (0.1% Tween, 20 mM Tris, 500 mM NaCl, pH 7.5) and incubated for 1 hour at room temperature or overnight in a 4° C. cold room. After blocking, the membranes were incubated with Mab31 (Chemicon Corp.) at a 1:5,000 dilution. The membranes were then washed 3 times at 5 minutes in TTBS and incubated with secondary antibody absorbed against human and mouse immunoglobulins and conjugated to horseradish peroxidase (HRP) at 1:10,000 dilution. The protein was visualized using enhanced chemiluminescence detection (NEN Life Science Products), with a typical exposure time of 1 minute. NBT/BCIP or streptavidin/biotin complex with alkaline phosphatase may also be used. Total protein in each sample was determined using the Bradford assay. Blots were scanned for densitometry using a Foto/Analyst® image analysis system with Collage™ software (Fotodyne, New Berlin, Wis.).

Figure 3A:
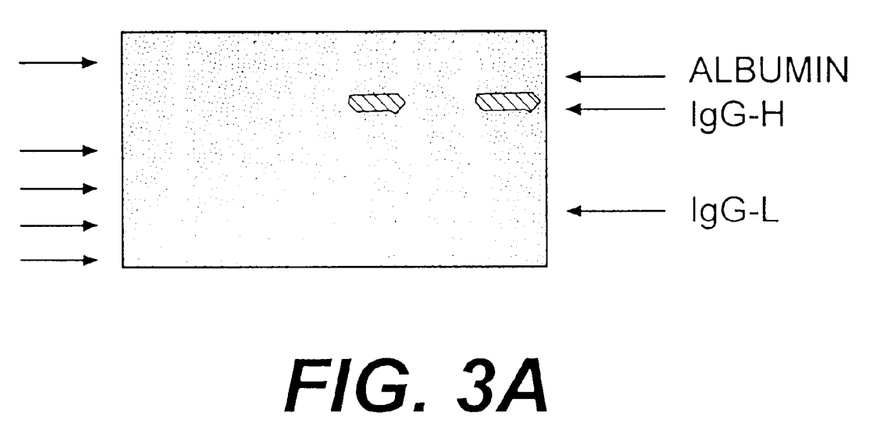
Figure 3B:
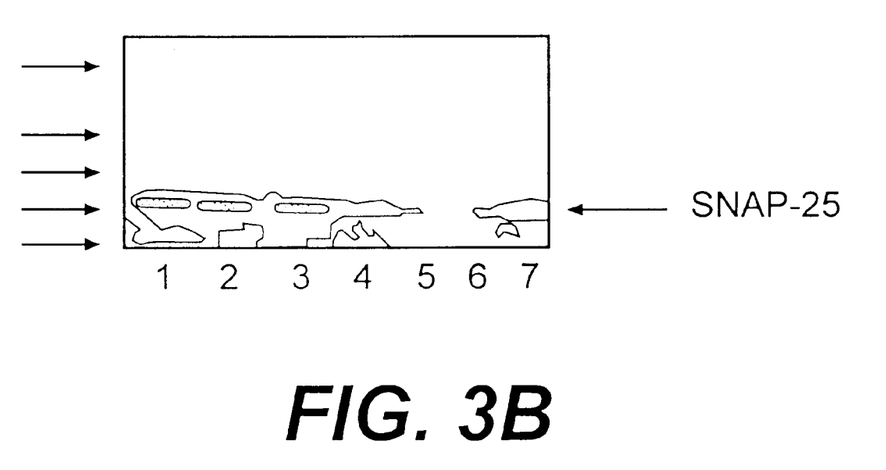
Figure 4:
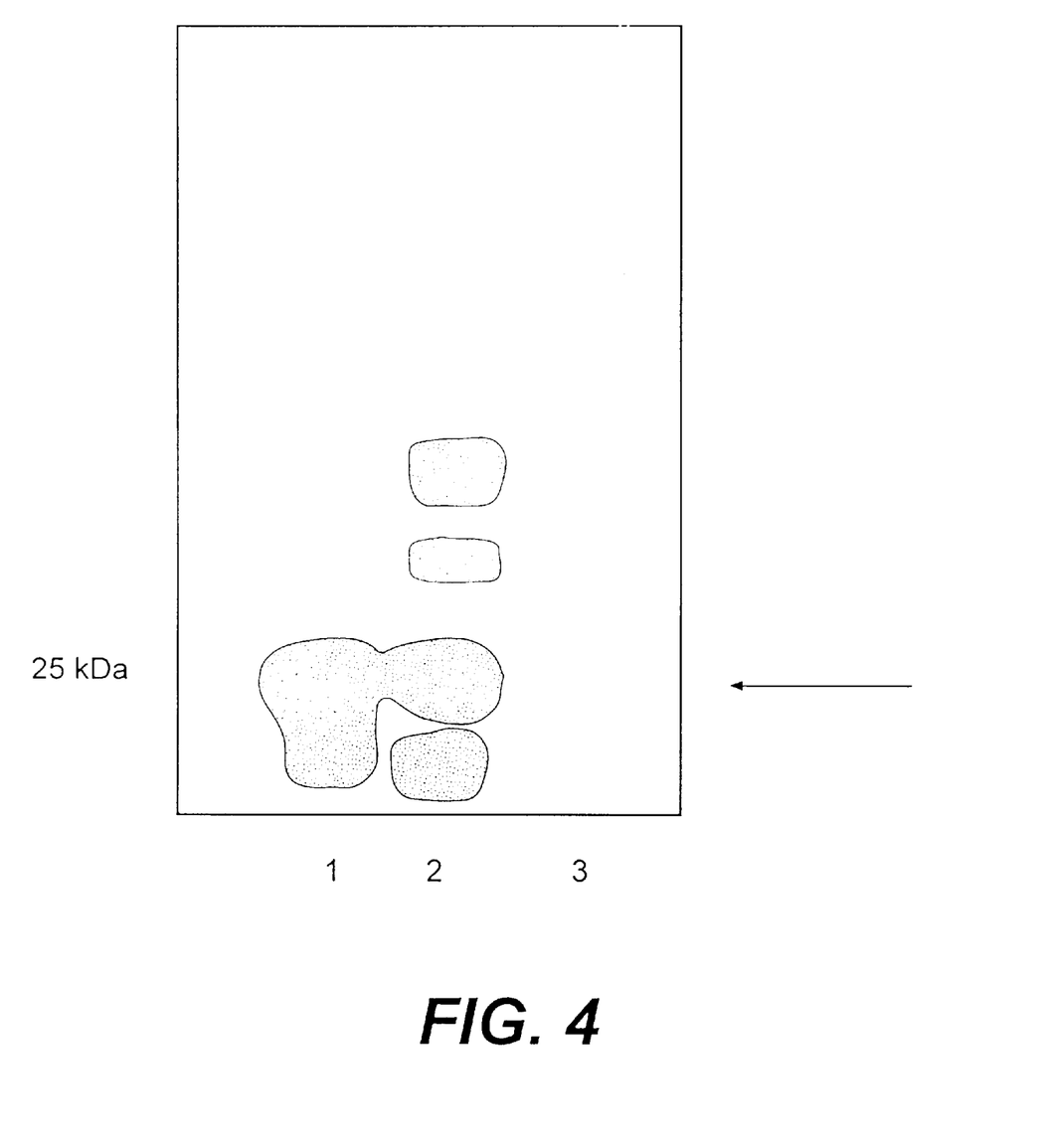
FIG. 4: Western blot of: Lane 1: rat brain homogenate; Lane 2: human brain homogenate; and Lane 3: AF (10 μl) with Mab SMI 81.

Control human brain samples were prepared as described in Thompson et al., (1997). Rat brain control is pooled brains from a litter of postnatal day 1 rats. The tissue was prepared as described in Benowit et al. (L. I. Benowit, P. J. Apostolides, N. I. Perrone-Bizzozero, S. P. Finklestein, and H. Zweirs., "Anatomical distribution of the growth associated protein GAP-43/B-50 in the adult rat brain." *J. Neurosci.* 8:339–352, 1988.). FIG. 1 shows that SNAP-25 levels are linear at the range tested and that this standard curve can be used to measure SNAP-25 levels in patients. FIG. 3 shows that when the CSF or AF is treated to remove various components SNAP-25 is unaffected and can continue to be identified.

Example VII

Dot Blot Analysis

Figure 5:
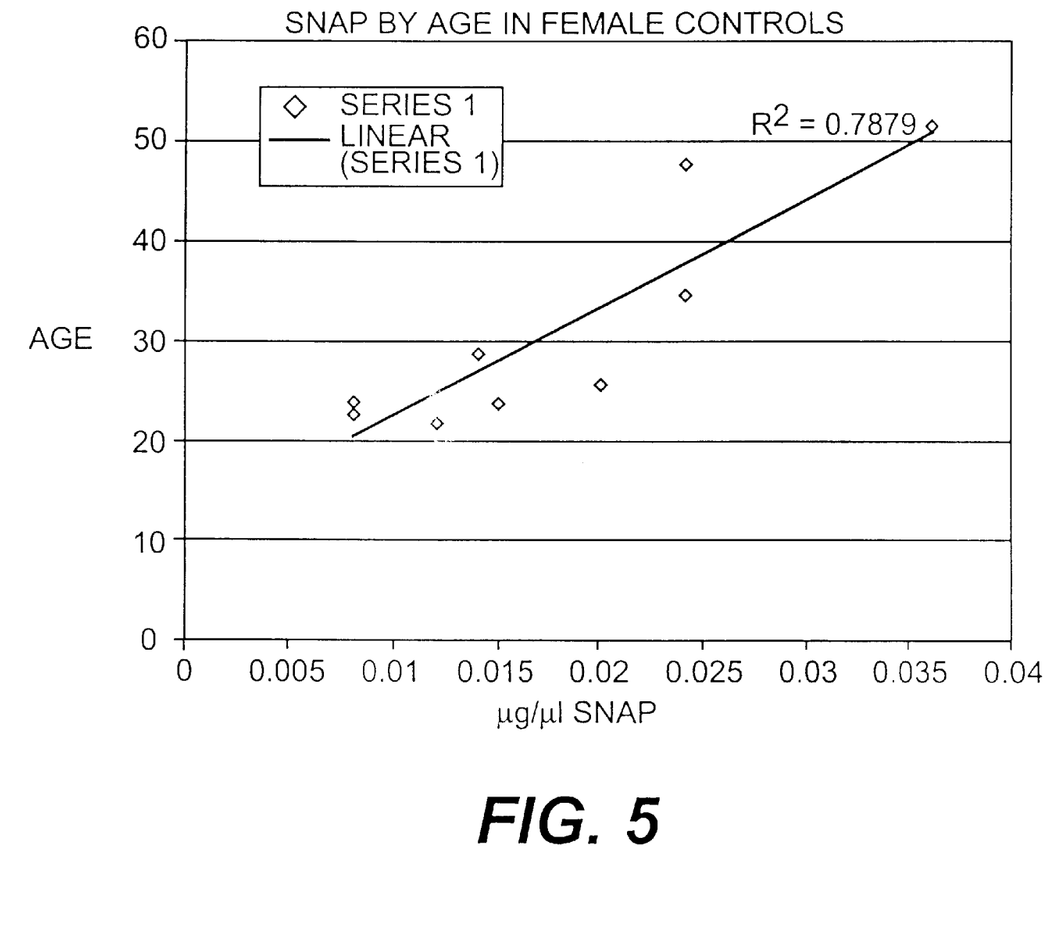
FIG. 5: Graph of SNAP-25 concentration (μg/μl CSF) plotted against age in female controls R=0.79.
Figure 6:
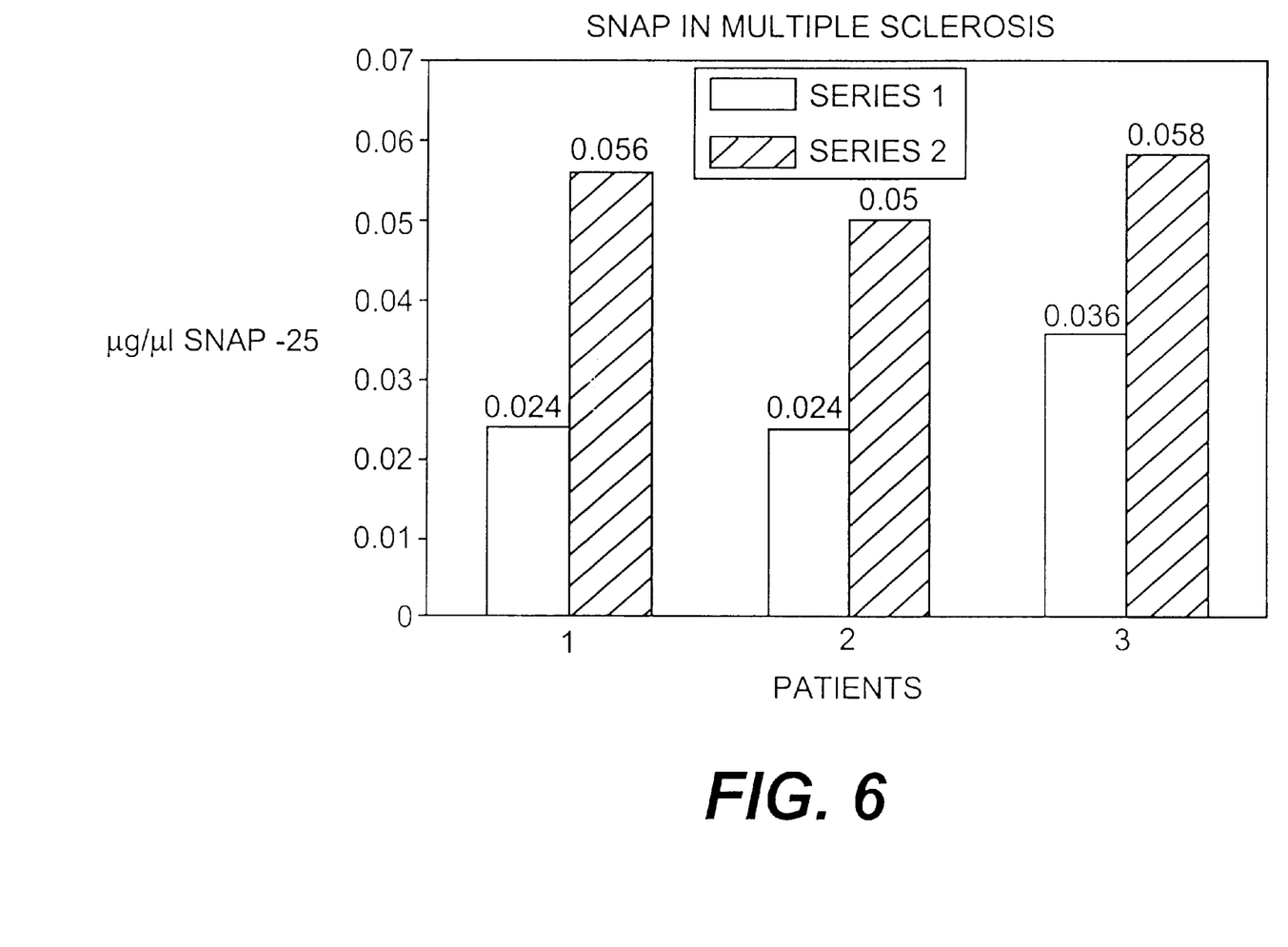
FIG. 6: Chart of four patients (series 2) with multiple sclerosis compared to age/sex matched controls (series 1).
Figure 7:
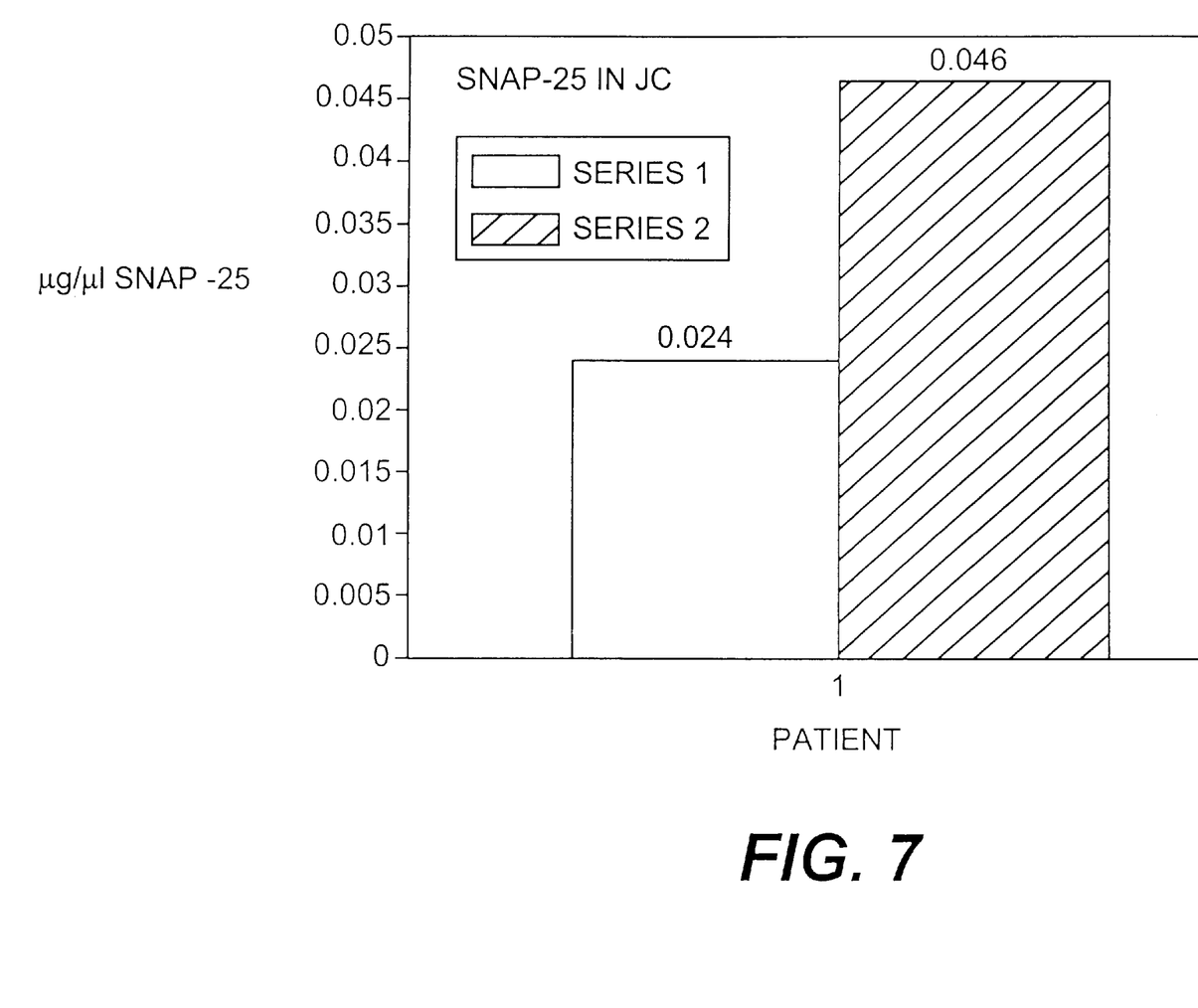
FIG. 7: Chart of a patient with Jakob Creutzfeldt disease and age/sex matched control.
Figure 8:
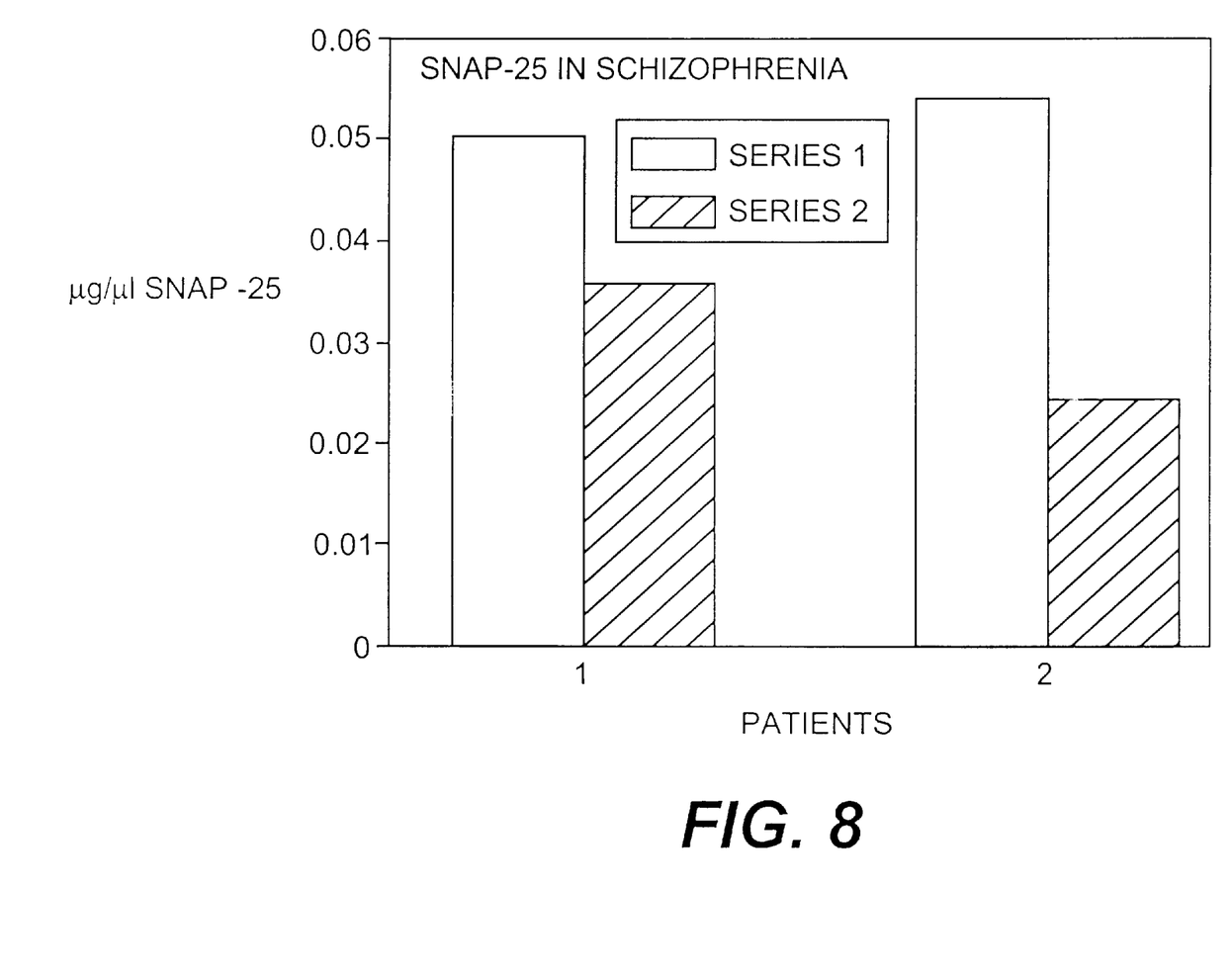
FIG. 8: Chart of 2 patients with schizophrenia compared with age/sex matched controls.

Dot blots were prepared by applying 50 µl, 2 µl, and 1 µl of fluid sample (CSF, AF or standard) to a PVDF membrane by light vacuum using a dot blot apparatus (BioRad Corp.). The resulting blot is then treated as western blot for immunodetection. FIG. 5 shows the linear relationship between SNAP-25 levels and age in female patients. FIG. 6 shows the SNAP-25 levels in controls who are age and sex matched compared to patients with multiple sclerosis. FIG. 7 shows the SNAP-25 level in a patient with Jakob Creutzfeldt disease and FIG. 8 SNAP-25 levels in schizophrenia.

Best Mode of Practicing the Invention

CSF or AF samples for analysis are collected as described supra, and purified with respect to albumin, preferably by adsorption on Blue Sepharose™ beads as described in Example II; the samples are then optionally concentrated with respect to total protein, for example, as described in Example III. The albumin-depleted samples are then purified with respect to immunoglobulins, particularly IgG, another predominant protein in these fluids which can significantly interfere with immunoanalysis of the sample for SNAP-25. This is preferably accomplished by adsorption on Protein G beads (Pharmacia Biotech).

SNAP-25 has been tentatively recognized as a major polypeptide component of a vesicular fusion particle comprising three major combined polypeptides and referred to as "D3 protein" (*Neurochem Res.* 20: 533–547, 536). It has been suggested that native SNAP-25 is present in this polypeptide composition in dimeric or oligomeric form complexed with other proteins. According to the present invention, SNAP-25 in the CSF or AF samples is isolated from this polypeptide complex prior to immunoassay, as it has been discovered that antibodies selective for SNAP-25 may not fully recognize the immunoreactive regions of SNAP-25 in its native configuration. Isolation is preferably done by full reduction of the SNAP-25 in the D3 polypeptide composition by processes known in the art. A particularly advantageous method is by treatment of the fluid samples with β-mercaptoethanol and dithiothreitol as set forth in Example VI. After reduction, the samples are immunoassayed for SNAP-25 and the amount of SNAP-25 in the sample quantitated. Exemplary immunoassays in addition to Western and dot blot include ELISA, RIA, and various other conventional assays employing immuno-labelled antibody, such as antibodies bound to alkaline phosphatase or fluorochrome. Conventional immunoassays are broadly useful.

Figure 1A:
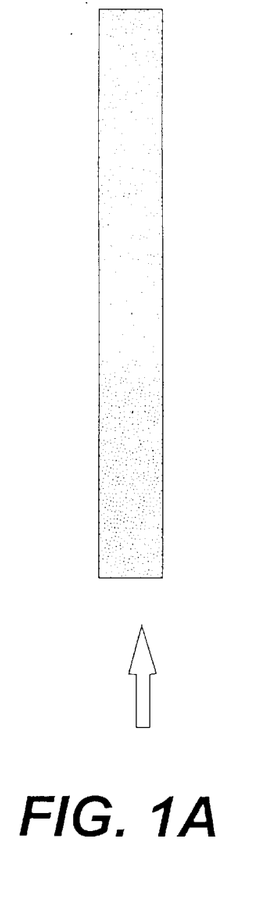
Figure 1B:
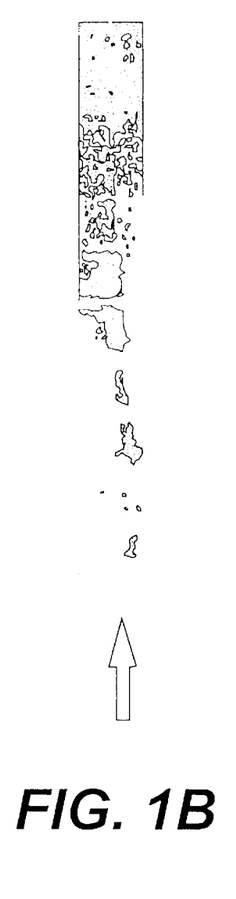
Figure 1C:
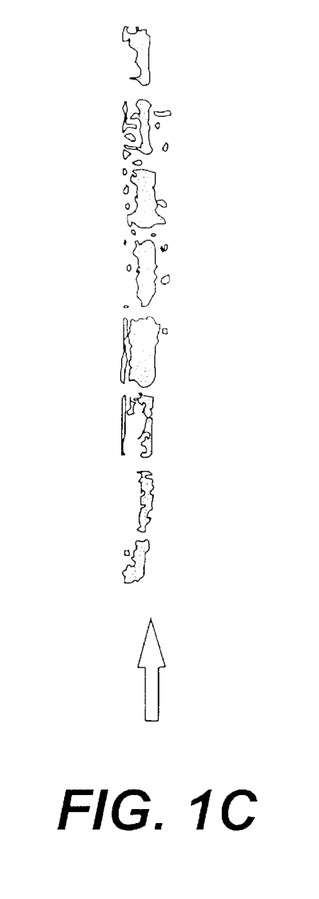
Figure 1D:
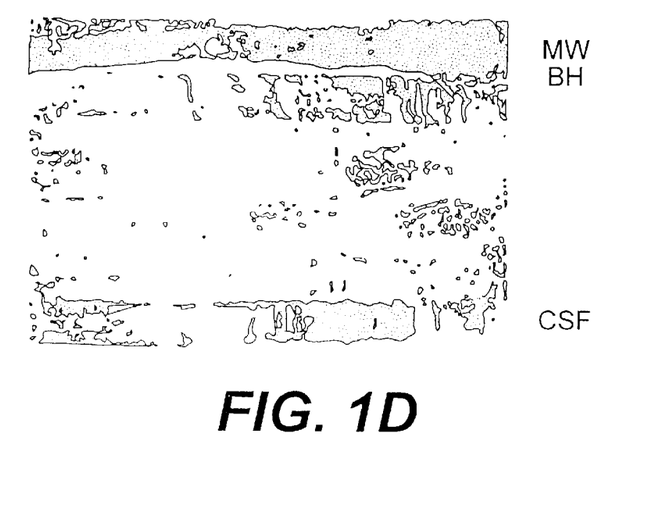
Figure 2:
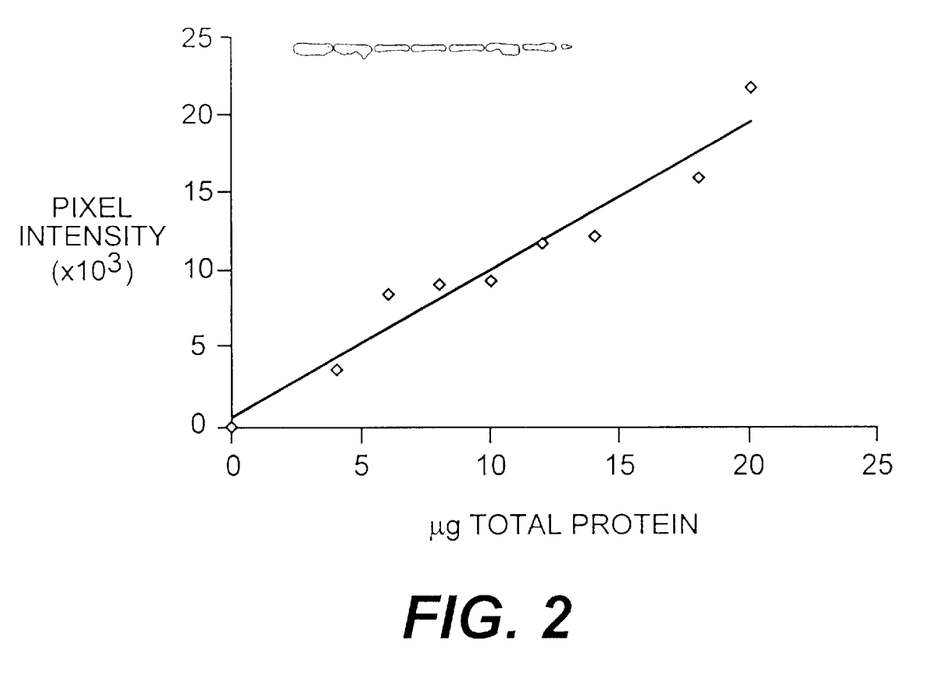
FIG. 2: Linear range and specificity of Mab33 in rat brain homogenate. Increasing amounts of homogenate (1–20 μg) were Western blotted. Relative band intensity was then plotted versus total protein.

For diagnosis of neurodisorders marked by SNAP-25 levels in CSF or AF, amounts of SNAP-25 in a given fluid sample are compared with controls unaffected by the disorder of interest. Quantitation (concentration) based, for example, on Western blot density can be determined by comparison of data to a standard curve such as illustrated in FIG. 2. Specificity of the antibodies can be confirmed by known techniques, such as running side-by-side controls as illustrated in FIG. 3.

What is claimed is:

1. A method for the identification and quantitation of synaptosomal associated protein-25 kDA (SNAP-25) in collected cerebrospinal or amniotic fluid comprising:

purifying the collected fluid with respect to albumin and immunoglobins, immunoprecipitating SNAP-25 with anti-SNAP-25 antibody to form SNAP25/anti-SNAP-25 antibody complexes, detecting said SNAP-25/anti-SNAP-25 antibody complexes, and quantitating said SNAP-25/anti-SNAP-25 antibody complexes.

2. The method of claim 1, wherein SNAP-25 is isolated from any proteins with which it is complexed in the collected fluid.

3. The method of claim 1, further comprising:

separating proteins in the collected fluid by molecular weight.

4. The method of claim 3, further comprising:

immobilizing the separated proteins.

5. The method of claim 4, wherein the proteins are immobilized on a polyvinylidene-difluoride membrane.

6. The method of claim 1, wherein the collected and purified fluid is immunoassayed by immobilization of protein on a support by dot blot or Western blot, and reacted with labeled anti-SNAP-25 antibody.

7. The method of claim 1, further comprising detecting and quantitating SNAP-25/anti-SNAP-25 antibody complexes formed by immunoprecipitating SNAP-25 with anti-SNAP-25 antibody.

8. An immunoprecipitated combination of SNAP-25 with anti-SNAP-25 antibody produced according to the method of claim 1.

* * * * *